United States Patent
Rawlings

[11] Patent Number: 5,385,542
[45] Date of Patent: Jan. 31, 1995

[54] TAMPON APPLICATORS

[75] Inventor: David A. Rawlings, Appleton-le-Moors, United Kingdom

[73] Assignee: Smith & Nephew plc, United Kingdom

[21] Appl. No.: 98,335
[22] PCT Filed: Feb. 10, 1992
[86] PCT No.: PCT/GB92/00238
 § 371 Date: Sep. 3, 1993
 § 102(e) Date: Sep. 3, 1993
[87] PCT Pub. No.: WO92/13508
 PCT Pub. Date: Aug. 20, 1992

[30] Foreign Application Priority Data

Feb. 12, 1991 [GB] United Kingdom ............ 9102928

[51] Int. Cl.$^6$ ............................................ A61F 13/20
[52] U.S. Cl. .................................... 604/14; 604/11; 604/15; 604/18; 604/904
[58] Field of Search ................ 604/11, 13, 14, 15, 604/16, 17, 18, 904

[56] References Cited

U.S. PATENT DOCUMENTS

| | | | |
|---|---|---|---|
| 2,587,717 | 3/1952 | Fourness | 604/18 |
| 3,101,713 | 8/1963 | Sargent | 604/16 |
| 4,573,963 | 3/1986 | Sheldon | 604/15 |
| 4,891,042 | 1/1990 | Melvin et al. | 604/18 |

FOREIGN PATENT DOCUMENTS

| | | | |
|---|---|---|---|
| 0121844 | 7/1946 | Australia | 604/18 |
| 0138491 | 5/1947 | Australia | 604/18 |
| 291343 | 11/1988 | European Pat. Off. | |
| 349222 | 1/1990 | European Pat. Off. | |
| 2204495 | 11/1988 | United Kingdom | |
| WO9106272 | 5/1991 | WIPO | |

Primary Examiner—Randall L. Green
Assistant Examiner—P. Zuttarelli
Attorney, Agent, or Firm—Rosenman & Colin

[57] ABSTRACT

A tampon applicator has an outer cylindrical member for containing a tampon and an inner arcuate member which is arranged to lie between the inner surface of the outer member and the tampon and to be slidably moved within the outer member to act as a piston for ejecting the tampon. One end of the inner member is adapted to engage the tampon and has a shoulder region. The outer member is provided with a first inward projection to engage the tampon and prevent rearward movement thereof and at least one second inward projection intermediate the first projection and the rear end of she cylindrical member to engage the shoulder region of the inner member and prevent complete withdrawal of she inner member from the outer member. The inward projections comprises at least one flap for example a pair of flaps or an inwardly deformed arcuate strip.

14 Claims, 3 Drawing Sheets

TAMPON APPLICATORS

The invention relates to tampon applicators. Conventional tampon applicators commonly comprise an outer cylindrical member for containing a catamenial tampon and an inner member which is adapted to slidably move within the outer member to act as a piston for ejecting the tampon. Such tampon applicators are often marketed in assembled form ready for use in which the tampon is provided towards one end of the outer member and the inner member is partially inserted within the other end of the outer member. It has been found, however, in general that the length of such assembled tampon applicators is inconvenient and awkward for storage in ladies handbags. For this reason, tampon applicators of compact form have been proposed in which the inner member is stored within the outer member alongside the tampon. Such applicators can be readily assembled for use by slidably moving the inner member rearwardly of the outer member to engage the rear of the tampon.

United Kingdom Patent Application GB 2033754A discloses a tampon applicator of compact form which comprises an outer cylindrical member for containing the tampon and an inner cylindrical member which lies between the tampon and the outer member and which can be slidably moved rearwardly therein from the tampons to engage the rear end thereof to form a piston for ejecting the tampon. The outer cylindrical member of this applicator has inward projections which can prevent withdrawal of the tampon and the inner cylindrical member when the inner member is moved rearwardly and the inner cylindrical member is provided with slots in which the projections can slidably engage. U.S. Pat. No. 3,090,385 discloses a similar tampon applicator of compact form which comprises an outer cylindrical member and an inner member which comprises a plurality of arms. The outer member of this applicator has inward projections to prevent withdrawal of the inner member and the tampon and the arms of the inner member comprise grooves in which the projections can slidably engage. The inner members of the tampon applicators disclosed in these patents, however, because of their construction, may be relatively complex or uneconomic to manufacture.

Tampon applicators have now been found which comprise an inner member of relatively simple construction which is economic to manufacture.

Accordingly the present invention provides a tampon applicator including an outer cylindrical member for containing a tampon and an inner arcuate member which is arranged to lie between the inner surface of the outer member and the tampon and to be slidably moved within the outer member to act as a piston for ejecting the tampon wherein one end of the inner member is adapted to engage the tampon and has a shoulder region and wherein the outer member is provided with a first inward projection to engage the tampon and prevent rearward movement thereof and at least one second inward projection intermediate the first projection and the rear end of the cylindrical member to engage the shoulder region of the inner member and prevent complete withdrawal of the inner member from the outer member, the distance between said first and second projections being such as to provide sufficient axial movement of the inner member to allow it to be slid rearwardly past the first projection before the shoulder region engages the second projection.

The tampon applicator of the invention employs an arcuate inner member which uses less material than a completely cylindrical inner member and is of a simple construction. The applicator thus comprises an inner member which is more economical to manufacture when compared to the inner members of hereinbefore disclosed tampon applicators of the prior art.

The circumference of the inner arcuate member can suitable subtend an angle of 90° to 270°, desirably an angle of 120° to 240° and can preferably subtend an angle of 150° to 220° for example an angle of 180°.

The inner arcuate member has a shoulder region or stepped portion which can be on one or both its longitudinal edges. It is preferred however, that the inner arcuate member has a stepped portion on both of its longitudinal edges to enable it to engage with a second inward projection on the outer cylindrical member comprising a pair of flaps or an inwardly deformed arcuate strip described hereinafter. The stepped portion will normally be positioned towards the front end of the inner arcuate member to be moved rearwardly past the rear end of the tampon before the stepped portion engages the second projection.

The ratio of the length of the stepped portion to the length of the inner arcuate member can suitably be less than 1:3, desirably less than 1:4 and can preferably be less than 1:5.

The step of the stepped portion should have a height which is sufficient to enable the step to engage with an inward projection such as a flap or strip of the outer cylindrical member. A step of a height of 1 to 5 mm has been found suitable to engage with an hereinafter mentioned flap or strip projection of the cylindrical member.

The arcuate inner member will normally have a similar length to that of the outer cylindrical member to provide the applicator with a compact form. The arcuate inner member is desirably longer than the outer cylindrical member to ensure that the inner member can eject a catamenial tampon through the end of the outer member which will be inserted into the vagina.

However, in order to maintain the compact form of the applicator the ratio of the length of the inner member to that of the outer member should be less than 1.3:1 desirably less than 1.2:1 and should preferably be less than 1.1 to 1.

The longer inner member preferably extends beyond the rear end of the outer member to provide the member at its rear end with a "handle" portion to facilitate grasping and slidably moving the inner member within the outer member. Such a "handle" portion of the arcuate member can favourably be a cylindrical portion to facilitate gripping the member. The rear end of the arcuate inner member can optionally be provided with a means to engage with the rear end or the second inward projection of the outer cylindrical member to prevent the inner member being initially moved forward when assembling the applicator. Such a means can favourably be a stepped portion which can engage with a second inward flap projection described hereinafter.

The arcuate inner member will have a front end which is adapted to engage the rear end of the tampon. The front end of the member can advantageously be provided with an abutment such as inwardly folded or curved portion to ensure engagement of the end with the tampon. Such a curved portion can favourably be resilient and segmented to allow the inner member to be moved rearwardly from the tampon to provide a piston for the applicator.

The outer cylindrical member has an end for insertion into the vagina. The outer cylindrical member may have a flat insertion end but it is preferred that this member has a segmented domed end to facilitate insertion of the member into the vagina. The domed end can aptly be segmented into petal shape segments which converge to a small central aperture at the front portion of the end. The segments or petals however, can be within, coextensive with or extend beyond the domed end portion of the cylindrical member.

Suitable segmented domed end cylindrical tubes for making the outer cylindrical members used in the applicators of the invention are disclosed in European Patent Application Nos. 0115193 and 0066212.

The rear end of the outer cylindrical member which is adjacent to the arcuate inner member when the applicator is in compact form can advantageously have an re-entrant portion to expose the rear end of the arcuate member to facilitate handling of the member when it is to be moved.

The outer cylindrical member has first and second inward projections to engage with the tampon or the stepped portion or portions of the inner member. Suitable inward projections include projections formed by methods such as adhering or moulding a small component for example a block on the inner surface of the cylindrical member or by deforming or cutting the wall of the cylindrical member to form a raised inner portion thereof. Favoured inward projections of the cylindrical member are flaps formed by example by cutting or by punching and folding a portion of the wall of the cylindrical member and an inwardly deformed arcuate strip portions of the cylindrical member.

In preferred embodiments of the invention the first and second inward projections each comprise one or more flaps for examples a pair of flaps or a inwardly deformed arcuate strip portion.

In a favoured embodiment of the invention which comprise flap projections the first and second inward projections each comprise a single flap or the first inward projection comprises a single flap and the second inward projection comprises a pair of flaps.

Such flaps can be axial or transverse flaps and can have any convenient shape such as rectangular triangular or curved shape provided it is suitable for engagement with the tampon or stepped portion of the arcuate member.

In another favoured embodiment of the invention the first and second inward projections each comprise an inwardly deformed arcuate strip portion of the outer cylindrical member.

The strip portion of both projections will normally lie perpendicular to the length or axial direction of the outer member. The deformed strip portion of at least the second projection will have a shape such as a curved or angled arched shape to enable the projection to engage with the pair of stepped portions on the arcuate member when this member is moved rearwardly of the outer member. Such a projection can be readily formed by cutting an arcuate strip of appropriate width and length in the outer cylindrical member and deforming the strip inwardly by means of a suitable tool such as rounded or angled edge flat tool.

In a further favoured embodiment of the invention the first and second projections each comprise a pair of opposed inwardly projecting flaps formed from an arcuate strip portion of the outer cylindrical member. Such inward projecting flaps can be readily formed by cutting an arcuate strip of appropriate width and length in the outer cylindrical member, cutting the strip preferably centrally in the axial direction of the outer member to form a pair of flaps and folding the flaps to project inwardly of the member.

The first and second inward flap or strip projections will normally be positioned towards the rear end of the outer member and in a portion thereof which is not in contact with the inner arcuate member or the tampon when the applicator is in compact form so as not to inhibit the sliding movement of the arcuate member during assembly of the applicator or when it is used as a piston to eject the tampon.

The first and second inward projections of the outer member can be in a position within the member which is central to or towards one or both longitudinal sides of the arcute inner member. It is preferred however when the projections are flaps that two of the first and second projections are positioned adjacent to opposite longitudinal sides of the arcuate inner member to act as a guide for the member and also prevent it rotating in use. When the inward projections so positioned comprise flaps formed by folding a cut portion of the inner member it is also preferred that the flaps fold away from the longitudinal sides of the stepped portion or portions of the arcuate member to prevent the flaps closing in when in contact with said sides or portions. The flaps can advantageously fold away from the longitudinal sides of the arcuate member so that this member covers the cut out portions of the inner member from which the flaps were formed.

It is essential, however, that the first inward projection or projections should not be capable of engaging with the stepped portion or portions of the arcuate member to prevent the member being slid rearwardly of the tampon. The first inward projection or projections will thus also be positioned in a portion of the cylindrical member which is not contacted by the arcuate member when it's moved rearwardly therein.

Furthermore, when the first inward projection comprises a pair of flaps or an inwardly deformed arcuate strip the angle subtended by the remaining portion of the outer member which is adjacent to the deformed strip or flap projections should be greater than that subtended by the pair of stepped portions of the inner member to ensure that the first inward projection or projections do not engage these stepped portions when the inner member is moved rearwardly of the tampon.

Similarly when second inward projection comprises a pair of flaps or an inwardly deformed strip the angle subtended by the remaining portion of the outer member adjacent to the deformed strip or flap projections should be less than that subtended by the pair of stepped portions of the inner member to ensure engagement of the these portions with second inward projection or projections when the inner member is moved rearwardly to complete withdrawal of the inner member.

In embodiments with such first and second inward projections the length of strip portion or the distance between fold lines of the pair flaps of the first inward projection will therefore be less than length of or distance between a similar strip portion or pair of flaps of the second projections. The first and second strip projection or flap projections can advantageously be positioned adjacent to each other at or towards the rear end of the outer member. The strip portions of the outer member from which adjacent projections are made can readily be formed by making only three cuts instead of four cuts in the outer member.

In the applicator of the invention when in compact form the first inward projection will normally be located adjacent or near to the rear end of the tampon so that the projection will engage with the tampon to prevent rearward movement thereof when the inner arcuate member is initially moved reawardly.

The second inward projection or projections will be positioned rearwardly of the first inward projection for example at or near the rear end of outer cylindrical member. The second projection or projections will also be positioned at an axial distance from the first projection which is equal or preferably greater than the axial length of the stepped portion to allow the inner member to be slid rearwardly past the point of contact of the first inward projection and hence the rear end of the tampon before the stepped portion or portions engage the second projection or projections. The second inward projection or projections so positioned will prevent complete withdrawal of the inner member from the outer member and also allow the inner member to be engaged with the rear end of the tampon and act as a piston for ejecting the tampon for the outer member.

The applicator of the invention can be made of any of the materials such as plastics, cardboard or paper used for conventional tampon applicators. Preferred applicators of the inventions, however, comprise paper such as cardboard.

The outer cylindrical member is preferably made of a stiff cardboard material which will not collapse when inserted into the vagina.

The arcuate inner member is preferably made of a less stiff thinner cardboard material providing that it is sufficiently stiff to enable the inner member to act as a piston to eject the tampon.

The catamenial tampon used in the applicator can be any of the catamenial tampons known in the art. Such tampons preferably have a rounded front end and comprise an absorbent cellulosic fibrous material which will expand laterally when exposed to menses. Tampons of this type are well known in the art.

Tampon applicators of the invention in compact form can be packaged within a bacteria-proof pouch and rendered sterile within the pack by a conventional sterilising method such as electron or gamma irradiation.

The invention will now be illustrated by the following drawings in which

Figure 1:
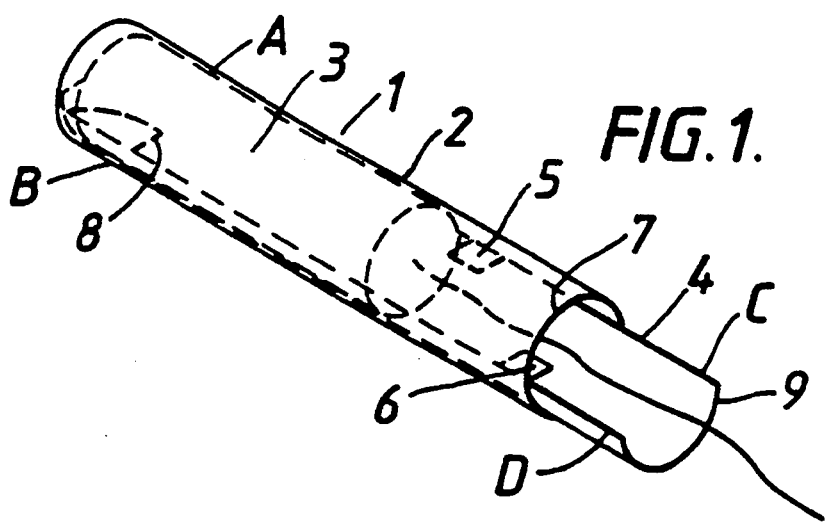
FIG. 1 is a perspective view of an applicator of the invention.
Figure 2:
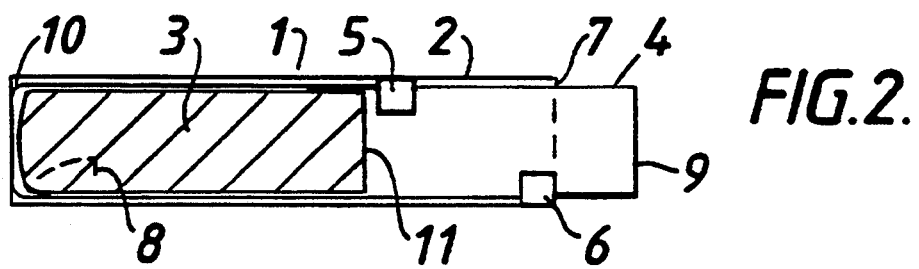
FIG. 2 is a cross section of the applicator of FIG. 1 along the plane A B C D.

FIGS. 1 and 2 show a tampon applicator of the invention in compact form which has an outer cylindrical member 2 containing tampon 3 and inner hemispherical member 4 which lies between the inner surface of outer member 2 and tampon 3 and which is adapted to be slidable moved within cylindrical member 2. Outer member 2 has inward projecting flap 5 to engage and prevent rearward movement of tampon 3 and another inward projecting flap 6 which is intermediate of flap 5 and the rear end 7 of the outer member 2. Flaps 5 and 6 are formed from the folded cut slot portions of the wall of outer member 2 beneath the flaps. As shown in FIG. 1 flaps 5 and 6 lie adjacent to the sides of inner member 4 to guide and prevent the member 4 rotating when it is slidably moved within outer member 2. Inner member 4 has a stepped portion 8 which can engage with flap 6 when inner member 4 is moved rearwards to prevent complete withdrawal of the inner member 4 from outer member 2. Inner member 4 also has a portion 9 at one end which extends beyond the rear end 7 of outer member 2 to act as a handle and a curved end 10 adapted to engage the rear end 11 of tampon 3.

Figure 3:
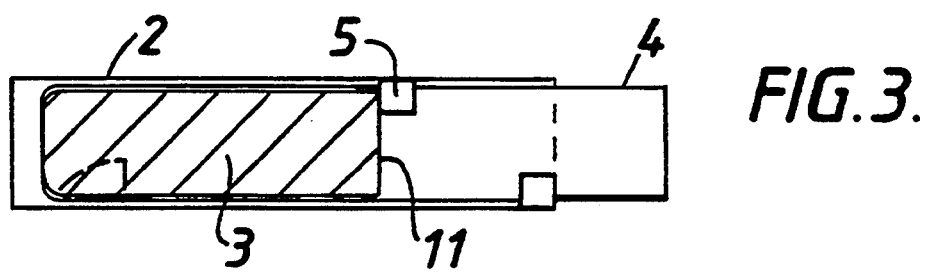
FIG. 3 is a similar cross section of the applicator of FIG. 1 with the inner member partially withdrawn.
Figure 4:
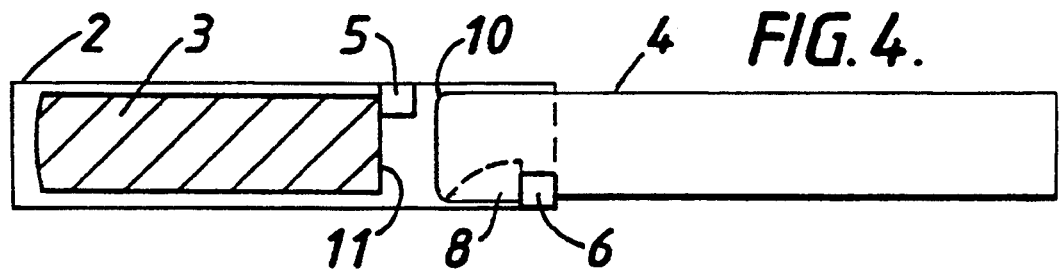
FIG. 4 is a similar cross section of the applicator of FIG. 1 ready for use.

In order prepare applicator 1 for use inner member 4 is first moved rearwardly within outer member 2 as shown in FIG. 3 to engage flap 5 with the rear end 11 of tampon 3. Inner member 4 is then moved further rearwardly within outer member 2 as shown in FIG. 4 to withdraw member 4 from tampon 3 and to engage stepped portion 8 with flap 6 to prevent complete withdrawal of inner member 4 from outer member 2. Inner member 4 can then be moved forward so that the front end 10 thereof is in contact with the rear end 11 of the tampon to provide a piston to eject the tampon from outer member 2. Applicator 1 can be used in a normal fashion to place tampon 3 into the vagina by inserting the front end of outer member 2 into the vagina, and ejecting tampon 3 from outer member 2 by means of inner member 4 and withdrawing members 2 and 4 from the vagina.

Figure 5:
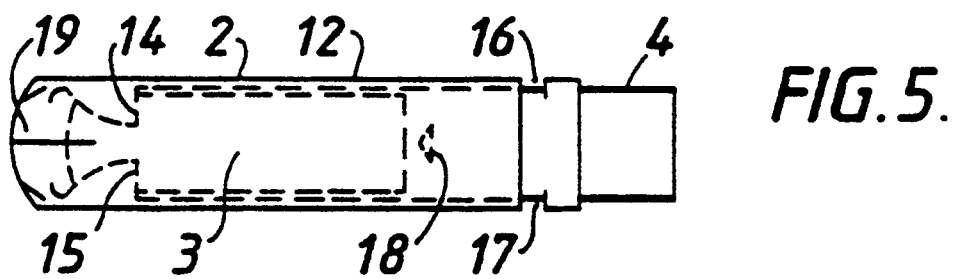
FIG. 5 is a schematic drawing of an elevated view of another applicator of the invention.

Applicator 12 shown in FIG. 5 is similar to that of applicator 1 shown in FIG. 1 except that arcuate inner member 4 has a pair of stepped portions 14 and 15 on opposite sides thereof and outer cylindrical member 2 has a pair of inward projecting flaps 16 and 17 which are adjacent to the sides of arcuate member 4 and which can engage with stepped portions 14 and 15 when arcuate member 4 is moved rearwardly. Outer cylindrical member 2 also has an inward projecting flap 18 located centrally with respect to the sides of arcuate member 4 which can engage the rear end 11 of tampon 3 to prevent rearward movement thereof. Flaps 16, 17 and 18 as shown in FIG. 5 are hinged radially of outer member 2 and fold away from the front end thereof. Such flaps can be aptly formed by punching the wall of outer member 2. Applicator 12 can be assembled for use and used to insert a tampon into the vagina in the same manner as applicator 1, outer cylindrical member 2 of applicator 12, however, is provided with a segmented domed end 19 to facilitate insertion of member 2 into the vagina.

Figure 6:
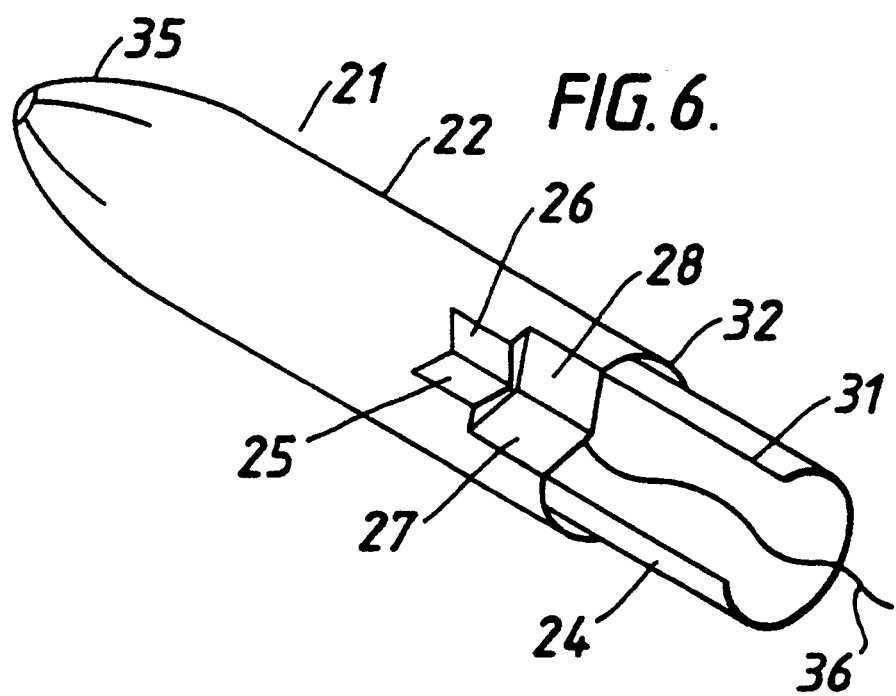
FIG. 6 is a perspective view of a further applicator of the invention.
Figure 7:
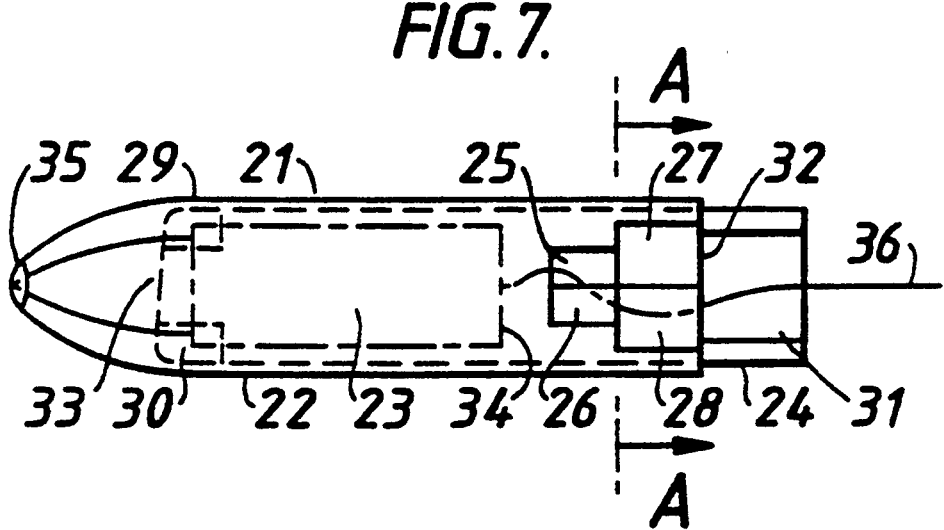
FIG. 7 is a plan view of the applicator of FIG. 6.

FIGS. 6 and 7 show a further tampon applicator 21 of the invention in compact form which has an outer cylindrical member 22 containing tampon 23 and inner hemispherical member 24 which lies between the inner surface of outer member 22 and tampon 23 and which is adapted to be slidable moved within cylindrical member 22. Outer member 22 has pair of opposed inward projecting flaps 25 and 26 to engage and prevent rearward movement of tampon 23 and another pair of opposed inward projecting flaps 27 and 28 which are intermediate of flap 25 and 26 and the rear end 32 of the outer member 22. Both pairs of flaps 25, 26 and 27, 28 are formed from axially cut and folded arcuate strip portions of the wall of outer member 22. Inner member 24 has a stepped portions 29 and 30 which can engage with flaps 27 and 28 when inner member 24 is moved rearwards to prevent complete withdrawal of the inner member 24 from outer member 22. As shown more clearly in FIG. 8 the angle subtended by the remaining portion of member 22 adjacent to flaps 25 and 26 is greater than that subtended by the remaining portion of member 22 adjacent to flaps 27 and 28 to ensure that flaps 25 and 26 do not engage with stepped portions 29 and 30 when member 24 is moved rearwardly of outer member 22. Inner member 24 also has a portion 31 at one end which extends beyond the rear end 32 of outer member 22 to act as a handle and a curved end 33 adapted to engage the rear end 34 of tampon 23. Outer member 22 has a segmented domed front end 35 to facilitate insertion thereof into a vagina. Tampon 23 is provided with a conventional withdrawal string 36.

In order to prepare applicator 21 for use inner member 24 is first moved rearwardly within outer member 22 to engage flaps 25 and 26 with the rear end 34 of tampon 23. Inner member 24 is then moved further rearwardly within outer member 22 to withdraw member 24 from tampon 33 and to engage stepped portions 29 and 30 with flaps 27 and 28 to prevent complete withdrawal of inner member 24 from outer member 22. Inner member 24 can then be moved forward so that the front end 33 thereof is in contact with the rear end 34 of the tampon to provide a piston to eject tampon 23 from outer member 22. Applicator 21 can be used in a normal fashion to place tampon 23 into the vagina by inserting the front end of outer member 22 into the vagina, and ejecting tampon 23 from outer member 22 by means of inner member 24 and withdrawing member 22 and 24 from the vagina.

The rear end of arcuate member 24 can be provided with cylindrical portion (not shown) to facilitate handling member 24 and which can engage with flaps 27 and 28 at rear end 32 of outer member 22 to prevent inner member 24 being initially moved forward during assembly of the applicator.

Figure 8:
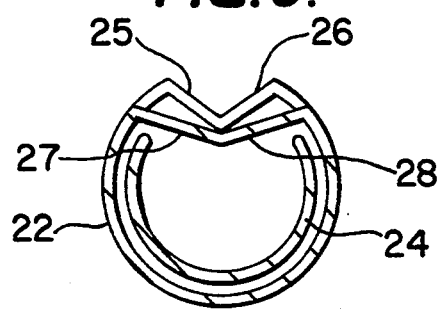
FIG. 8 is a cross section of the applicator shown in FIG. 7 along the line A—A.
Figure 9:
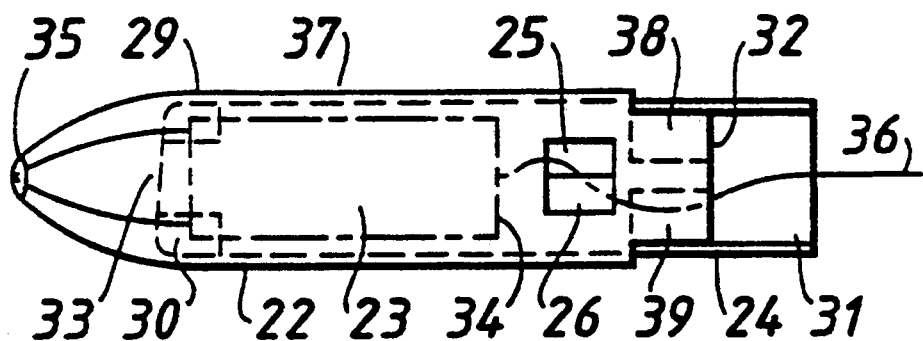
FIG. 9 is a plan view of yet another applicator of the invention.
Figure 10:
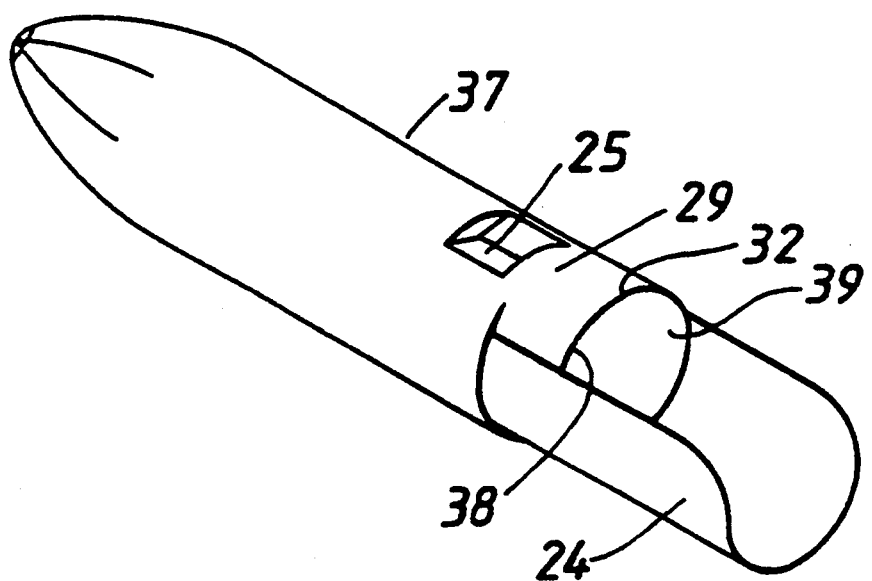
FIG. 10 is a perspective view of the applicator showing in FIG. 9.

FIGS. 9 and 10 show another tampon applicator 37 similar to that of FIGS. 6 to 8 except that rear end 32 of outer cylindrical member 29 has inwardly projecting flaps 38, 39 formed from the lower portion of member 29 so that inner hemispherical member 24 now encloses flaps 38, 39.

The stepped portions 29 and 30 engage with flaps 38, 39 when inner member 24 is moved rearwards to prevent complete withdrawal of inner member 24 from outer member 29.

The inner arcuate members 4 and 24 of applicators 1, 12, 21 and 37 thus have a relatively simple construction which uses less material than the cylindrical inner members or are less complex than the inner members comprising a plurality of arms used in prior art compact applicators.

I claim:

1. A tampon applicator including an outer cylindrical member for containing a tampon having a front end through which a tampon can be ejected and a rear end, and an inner arcuate member which is arranged to lie between an inner surface of the outer member and the tampon and to be slidably moved within the outer member to act as a piston for ejecting the tampon wherein one end of the inner member is adapted to engage the tampon and has an extending shoulder and wherein the outer member is integrally provided with a first inward projection to engage the tampon and prevent rearward movement thereof and at least one second inward projection at a distance from the first inward projection and intermediate the first projection and the rear end of the cylindrical member to engage the shoulder of the inner member and prevent complete withdrawal of the inner member from the outer member, the distance between said first and second projections being such as to provide sufficient axial movement of the inner member to allow it to be slid rearwardly past the first projection before the shoulder engages the second projection.

2. An applicator as claimed in claim 1 in which at least one of the inward projections comprises a flap.

3. An applicator as claimed in claim 2 in which the flap has an axis which lies in the axial direction of the outer cylindrical member.

4. An applicator as claimed in claim 1 in which at least one of the inward projections comprises a pair of opposed inwardly directing flaps which are positioned within the outer cylindrical member adjacent to the longitudinal sides of an arcuate member.

5. An applicator as claimed in claim 1 in which the first and second inward projections each comprise a pair of flaps.

6. An applicator as claimed in claim 1 in which at least one of the inward projections comprises an inwardly deformed arcuate strip.

7. An applicator as claimed in claim 1 and 6 in which the first inward projection comprises an inwardly deformed arcuate strip and the second inward projection comprises a pair of flaps.

8. An applicator as claimed in claim 1 in which the inner arcuate member comprises a shoulder on both its longitudinal edges.

9. An applicator as claimed in claim 1 in which a shoulder of the inner arcuate member comprises a stepped portion for engagement with an inward projection.

10. An applicator as claimed in claim 1 in which the front end of the inner arcuate member comprise abutment to ensure engagement of the end with a tampon.

11. An applicator as claimed in claim 1 in which the inner arcuate member extends beyond the rear end of the outer member to a provide a handle therefor.

12. An applicator as claimed in claim 1 in which outer member comprises a segmented domed insertion end.

13. An applicator as claimed in claim 1 containing a catamenial tampon within the outer member.

14. A sterile applicator as claimed in claim 1 within a bacteria-proof pack.

* * * * *